United States Patent [19]
Knöfel et al.

[11] Patent Number: 4,761,498

[45] Date of Patent: Aug. 2, 1988

[54] DIISOCYANATES AND DIISOCYANATE MIXTURES BASED ON DIPHENYLMETHANE, PROCESSES FOR THEIR PRODUCTION AND THEIR USE AS ISOCYANATE COMPONENT IN THE PRODUCTION OF POLYURETHANE PLASTICS BY THE ISOCYANATE POLYADDITION PROCESS

[75] Inventors: Hartmut Knöfel, Odenthal; Michael Brockelt, Bergisch-Gladbach; Gerhard Wegener, Wuppertal, all of Fed. Rep. of Germany

[73] Assignee: Bayer Aktiengesellschaft, Leverkusen, Fed. Rep. of Germany

[21] Appl. No.: 28,265

[22] Filed: Mar. 20, 1987

Related U.S. Application Data

[63] Continuation of Ser. No. 360,856, Mar. 22, 1982, abandoned, which is a continuation of Ser. No. 182,569, Aug. 29, 1980, abandoned.

[30] Foreign Application Priority Data

Aug. 31, 1979 [DE] Fed. Rep. of Germany ....... 2935318

[51] Int. Cl.$^4$ .................. C07C 118/00; C08G 18/00
[52] U.S. Cl. ..................... 560/359; 521/155
[58] Field of Search ......................... 560/359

[56] References Cited

U.S. PATENT DOCUMENTS

| | | | |
|---|---|---|---|
| 3,152,162 | 10/1964 | Fischer et al. | 260/453 |
| 3,180,883 | 4/1965 | Case | 560/359 |
| 3,375,264 | 3/1968 | Sayigh et al. | 260/453 |
| 3,526,652 | 9/1970 | Powers | 560/359 |
| 3,644,457 | 2/1972 | Konig et al. | 260/453 |
| 4,014,914 | 3/1977 | Pistor et al. | 260/453 PH |
| 4,189,354 | 2/1980 | Ellendt et al. | 203/81 |

*Primary Examiner*—Alan Siegel
*Attorney, Agent, or Firm*—Gene Harsh; Joseph C. Gil

[57] ABSTRACT

The instant invention is directed to diisocyanates based on diphenylmethane which may be methyl-substituted and which are characterized in particular by isocyanate groups in the 3,4'- and optionally in the 3,2'-position. The instant invention is also directed to a number of independent processes for their production and to their use as isocyanate component in the production of polyurethanes.

6 Claims, No Drawings

DIISOCYANATES AND DIISOCYANATE MIXTURES BASED ON DIPHENYLMETHANE, PROCESSES FOR THEIR PRODUCTION AND THEIR USE AS ISOCYANATE COMPONENT IN THE PRODUCTION OF POLYURETHANE PLASTICS BY THE ISOCYANATE POLYADDITION PROCESS

This application is a continuation of application Ser. No. 360,856, filed Mar. 22, 1982, now abandoned, which itself is a continuation of application Ser. No. 182,569, filed Aug. 29, 1980 (now abandoned).

BACKGROUND OF THE INVENTION

This invention relates to new diisocyanates based on diphenylmethane which may be methyl-substituted and which are characterized, in particular, by isocyanate groups in the 3,4'- and, optionally, in the 3,2'-position. The instant invention also relates to a number of processes for their production and to their use as isocyanate component in the production of polyurethane plastics by the isocyanate polyaddition process.

Among the organic polyisocyanates of commercial and economic significance as starting materials for polyurethane plastics, 2,4-diisocyanatotoluene or mixtures thereof with 2,6-diisocyanatotoluene (TDI) and 4,4'-diisocyanatodiphenylmethane or mixtures thereof with 2,2'- or 2,4'-diisocyanatodiphenylmethane and/or with higher homclogs (MDI) are particularly important. Although these aromatic polyisocyanates are universally used in large quantities for the production of polyurethane plastics, particularly foams and elastomers, their use involves certain disadvantages. Thus, TDI, for example, has an increased vapor pressure in comparison with MDI, which means that, for physiological reasons, appropriate safety measures have to be strictly observed in the processing of this raw material. On the other hand, MDI, i.e. in particular, the 4,4'-diisocyanatodiphenylmethane generally present as main component in polyisocyanate mixtures based on diphenylmethane, is a solid at room temperature with a pronounced tendency towards crystallization. Before processing, these raw materials have to be liquified either by heating to a temperature above the melting point of 4,4'-diisocyanatodiphenylmethane or by chemical modification, for example partial urethane formation (U.S. Pat. No. 3,644,457) or partial carbodiimide formation (U.S. Pat. No. 3,152,162).

The present invention provides new aromatic polyisocyanates which combine the advantages of TDI and MDI without having any of their disadvantages. In addition, the new diisocyanates and diisocyanate mixtures, in contrast to 4,4'-diisocyantodiphenylmethane, contain isocyanate groups of different reactivity which is often of advantage in the production of polyurethane plastics. In addition, the use of the new diisocyanates or diisocyanate mixtures according to the invention in the production of polyurethane plastics makes it possible for new rigid segments corresponding to the hydrocarbon skeleton of the diisocyanates to be incorporated into the polyurethane plastics, which provide a new and interesting possibility for variation in the production of polyurethane plastics.

DESCRIPTION OF THE INVENTION

The present invention relates to diisocyanates corresponding to the formula:

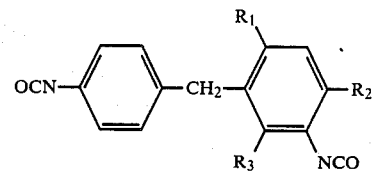

which may be in admixture with 0 to 40% by weight, based on the total mixture, of diisocyanates corresponding to the following formual:

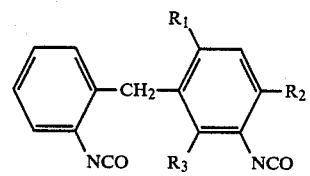

and which may be in admixture with 0 to 30% by weight, based on the total mixture, of other optionally methyl-substituted diisocyanatodiphenylmethane isomers; in the above formulae, the radicals $R_1$, $R_2$ and $R_3$, which may be the same or different, represent hydrogen or a methyl group, with the proviso that, in each of the two formulae, at least two of the radicals $R_1$, $R_2$ and $R_3$ represent hydrogen and one of the radicals $R_1$, $R_2$ or $R_3$ is preferably a methyl group.

The above definition for $R_1$, $R_2$ and $R_3$ applies throughout the specification.

The present invention also relates to the following diisocyanate:

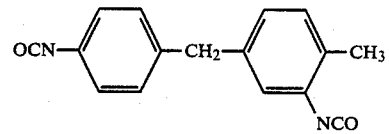

which is present as the main component in these diisocyanates or diisocyanate mixtures and which may also be prepared in pure form, and to the following diisocyanate

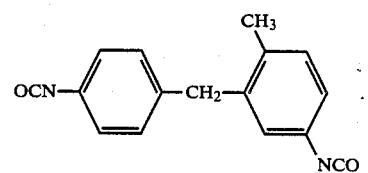

The invention also relates to the processes described hereinafter for produciing the new diisocyanates or diisocyanate mixtures and to the use of the new diisocyanates or diisocyanate mixtures as isocyanate component in the production of polyurethane plastics by the isocyanate polyaddition process.

The foregoing and following observations on the composition of the mixtures according to the invention and on the starting materials and intermediate products are based on values determined by gas chromatography.

The first process according to the invention for producing diisocyanates according to the invention, comprises:

(a) reacting a 4-nitrobenzyl halide with nitrobenzene and/or o-nitrotoluene and/or p-nitrotoluene in the presence of a Friedel-Crafts catalyst to form dinitro compounds corresponding to the following formula:

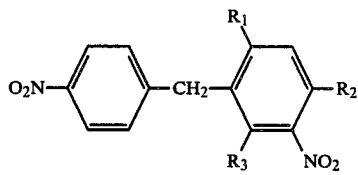

wherein $R_1$, $R_2$ and $R_3$, which may be same or different, represent hydrogen or a methyl group, with the proviso that at least two of the radicals $R_1$, $R_2$ and $R_3$ represent hydrogen, and freeing the reaction product obtained from the catalyst used;

(b) hydrogenating or reducing the nitro groups of the reaction product obtained in stage (a) into the corresponding aromatic diamino compounds;

(c) phosgenating the diamino compounds obtained in accordance with (b) into the diisocyanates; and (d) optionally isolating the corresponding 3,4'-diamino or 3,4'-diisocyanato isomers by distillation free from secondary products from the diamines obtained in accordance with (b) before the phosgenation reaction and/or from the diisocyanates obtained in accordance with (c).

Both here and in the following, "nitrobenzyl halide" and "benzyl halide" are understood to be in particular corresponding benzyl chlorides or bromides, most particularly the correspoonding benzyl chlorides.

In stage (a) of the first process according to the invention, a Friedel-Crafts condensation reaction takes place between 4-nitrobenzyl halide and nitrobenzene and/or o-nitrotoluene and/or p-nitrotoluene. The reactants are used in such quantities that from 1.0 to 20 mols and preferably from 2 to 10 mols of nitrobenzene and/or nitrotoluene are available for each mol of nitrobenzyl halide. The component used in excess simultaneously serves as solvent. The catalysts used are the usual Friedel-Crafts catalysts, for example aluminum chloride, iron trichloride, titanium tetrachloride or tin tetrachloride. Iron trichloride is preferably used as catalyst. The catalysts are generally used in quantities of from 1 to 100 mol percent, preferably from 5 to 50 mol percent, based on the benzyl halide component. The reaction is generally carried out at a temperature between room temperature and the boiling point of the reaction mixture, i.e. at a temperature of from about +20° to about 200° C. and preferably at a temperature of from 30° to 120° C. On completion of the condensation reaction, the catalyst is removed, preferably by washing out, for example with water and, optionally, dilute hydrochloric acid and the excess, unreacted starting material is distilled off.

Thereafter, the nitro groups are reduced in stage (b) into the corresponding aromatically bound amino groups. This reduction stage is perferably carried out by catalytic hydrogenation, for example using Raney nickel or palladium as catalyst. Hydrogenation is generally carried out in alcoholic solution, methanol, ethanol or isopropanol, for example, being used as the solvent. The nitro compounds to be hydrogenated are generally used in the form of a 10 to 50% by weight solution. Hydrogenation is carried out, optionally under pressure, at a temperature of from 20° to 150° C. and preferably at a temperature of from 30° to 100° C. Conversion of the nitro groups into the corresponding amino groups may, of course, also be carried out by the reduction method known per se using iron, zinc or tin, for example, as the reducing agent. After the nitro groups have been converted into the corresponding amino groups, the catalyst is removed, for example by filtration, and the solvent distilled off. The amine obtained as residue may then be subjected without further treatment to reaction stage (c). Where it is important to produce particularly pure products, the diamine or diamine mixture constitutionally corresponding to the process products according to the invention may also be produced by distillation free from secondary products from the amine mixture obtained in stage (b) before it is subjected to stage (c). Both here and in the following, "secondary products" are understood to be unidentified constituents which boil at lower and/or higher temperatures than the products or intermediate products according to the invention.

The diamines which may be purified by distillation are subsequently converted in stage (c) into the corresponding diisocyanates by phosgenation in known manner. The solvent used for this purpose may be chlorobenzene or dichlorobenzene, for example. Finally, after the auxiliary solvent has been distilled off, the process products according to the invention are left as residue and, if desired, may be obtained free from any secondary products still present by distillation.

Where nitrobenzene is used as the starting material, the first process according to the invention makes it possible for 3,4'-diisocyanatodiphenylmethane to be produced. Where nitrotoluene is used as the starting material, as is preferably the case, isomer mixtures containing from about 30 to 50% by weight of 3,4'-diisocyanato-2-methyl diphenylmethane and from about 50 to 70% by weight of 3,4'-diisocyanato-4-methyl diphenylmethane are formed in the case of o-nitrotoluene while 3,4'-diisocyanato-6-methyl diphenylmethane is formed in the case of p-nitrotoluene. 3,4'-diisocyanato-4-methyl diphenylmethane may be produced in pure form using the principle of the first process according to the invention, for example by producing the 3,4'-dinitro-4-methyl diphenylmethane in pure form by partial crystallization from the intermediate product obtained in (a) and its further reaction in accordance with (b) and (c). This purification by crystallization at the nitro stage is carried out, for example, by dissolving the mixture of nitro compounds based on 4-nitrobenzyl halide and o-nitrotoluene obtained after the removal of excess starting material by distillation in boiling alcohol or ethyl acetate to form a saturated solution and allowing the solution thus formed to cool to room temperature. The required isomer preferentially crystallizes out during cooling. The crystallization process may, of course, be repeated as many times as required.

The second process according to the invention for producing diisocyanates or diisocyanate mixtures comprises:

(a) reacting a 4-nitrobenzyl halide with toluence in the presence of a Friedel-Crafts catalyst to form a mixture of mononitro compounds of the formula:

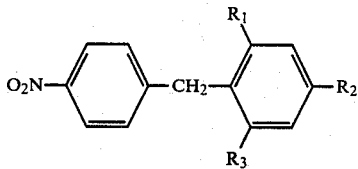

wherein $R_1$, $R_2$ and $R_3$, which may be the same or different, represent hydrogen or a methyl group, with the proviso that at least two of the radicals $R_1$, $R_2$ and $R_3$ represent hydrogen, and freeing the reaction product from the catalyst;

(b) nitrating the reaction product obtained in accordance with (a) to form dinitro compounds of the formula:

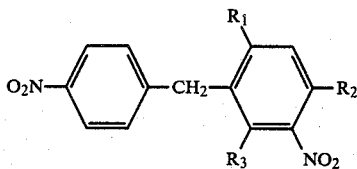

wherein $R_1$, $R_2$ and $R_3$ are as defined above;

(c) hydrogenating or reducing the amino groups of the dinitro compounds obtained in accordance with (b) into the corresponding aromatic diamino compounds; and (d) phosgenating the diamino compounds obtained in accordance with (c) into the corresponding diisocyanates;

(e) optionally, isolating the corresponding 3,4'-diamino or 3,4'-diisocyanato isomers free from secondary products by distillation from the diamines obtained in accordance with (c) before the phosgenation reaction and/or from the diisocyanates obtained in accordance with (d).

Stage (a) of the second process according to the invention corresponds to stage (a) of the first process according to the invention, except for the use of toluene as starting material. However, the boiling temperature of the toluene which, in this case, is used in an appropriate excess generally represents the upper limit of the temperature range. The condensation product obtained in stage (a) and free from the catalyst is subsequently nitrated in known manner in stage (b) to form a mixture of isomeric dinitro compounds corresponding to the above general formula. This nitration reaction is preferably carried out in the presence of a suitable solvent such as, for example, methylene chloride using "nitration acid", i.e. a mixture of concentrated sulfuric acid and nitric acid, preferably highly concentrated (approximately 98%) nitric acid. The nitration acid is used in such a quantity that approximately 1.1 mol of nitric acid is available for each mol of mononitro compound obtained in stage (a). Nitration is generally carried out at temperatures in the range from −20° to +80° C. and preferably at temperatures in the range of 0° to 20° C. The organic phase present after the nitration reaction is then freed from the acid by phase separation, washing with water and, for example, sodium carbonate solution. Finally, the auxiliary solvent is removed by distillation and any solvent residues left are subsequently removed by stripping with steam.

The further reaction of the dinitro compounds thus obtained is carried out in exactly the same way as described with reference to stages (b) and (c) of the first process according to the invention.

In the second process according to the invention, mixtures containing approximately 70 to 90% by weight of 3,4'-diisocyanato-2-, -4- or -6-methyl diphenylmethane and 10 to 30% by weight of other, analytically unidentified, methyl-substituted diisocyanato diphenylmethane isomers are generally formed as the diisocyanate mixtures according to the invention. Accordingly, the diisocyanates substantially correspond to the following formula:

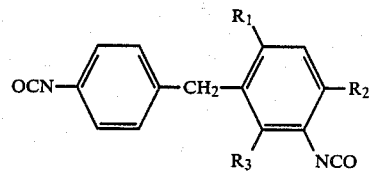

in which one of the radicals $R_1$, $R_2$ or $R_3$ represents a methyl group while the other two represent hydrogen.

The third process according to the invention for producing diisocyanates or diisocyanate mixtures according to the invention comprises:

(a) reactiing a 3-nitrobenzyl halide with benzene in the presence of a Friedel-Crafts catalyst to form 3-nitrodiphenylmethane and removing the catalyst from the reaction product;

(b) nitrating the nitro compound obtained in accordance with (a) to form 3,4'-dinitrodiphenylmethane containing up to 40% by weight of 2',3-dinitrodiphenylmethane;

(c) hydrogenating or reducing the nitro groups of the dinitro compounds obtained in accordance with (b) into the corresponding aromatic diamino compounds;

(d) phosgenating the diamino compounds obtained in accordance with (c) into the corresponding diisocyanates;

(e) optionally isolating the pure 3,4'-isomer or mixtures thereof with up to 40% by weight of 2',3-isomers in pure form from the amino compounds obtained in accordance with (c) before their phosgenation or from the polyisocyanates obtained in accordance with (d).

The third process according to the invention corresponds exactly to the second process described above apart from the use of different starting materials. The end product obtained is 3,4'-diisocyanatodiphenylmethane containing up to 40% by weight and generally from 20 to 30% by weight, based on the total mixture, of 2,3'-diisocyanatodiphenylmethane.

The fourth process according to the invention comprises:

(a) reacting toluene with commercial nitrobenzyl chloride isomer mixtures obtained by nitrating benzyl chloride and containing from 10 to 50% by weight, based on the total mixture, of 2-nitrobenzyl chloride and from 50 to 90% by weight, based on the total mixture, of 4-nitrobenzyl chloride together with small quantities of 3-nitrobenzyl chloride in the presence of Friedel-Crafts catalysts to form a Friedel-Crafts condensate containing mononitro compounds corresponding to the formulae:

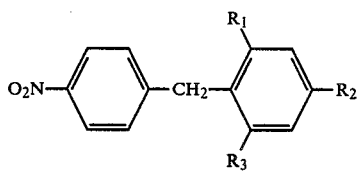

and

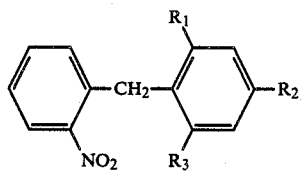

wherein $R_1$, $R_2$ and $R_3$, which may be the same or different, represent hydrogen or a methyl group, with the proviso that at least two of the radicals $R_1$, $R_2$ and $R_3$ in each formula represent hydrogen, and removing the catalyst from the condensate;

(b) nitrating the condensate obtained in stage (a) to form a mixture of aromatic dinitro compounds containing nitro compounds corresponding to the formulae:

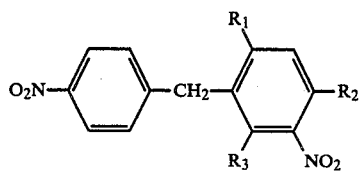

and

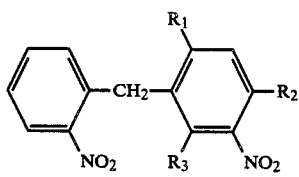

wherein $R_1$, $R_2$ and $R_3$ are as defined above;

(c) hydrogenating or reducing the nitro groups of the nitro compounds obtained in stage (b) into the corresponding aromatic diamines;

(d) phosgenating the diamines obtained in stage (c) into the corresponding diisocyanates;

(e) optionally isolating free from secondary products by distillation the isomer mixture containing from 30 to 60% by weight, based on the total mixture, of 3,4'-isomers and from 10 to 40% by weight, based on the total mixture, of 3,2'-isomers and from 0 to 30% by weight, based on the total mixture of other methyl-substituted diisocyanatodiphenylmethane isomers from the mixture of aromatic amino compounds obtained in accordance with (c) before phosgenation and/or from the polyisocyanate mixture obtained in accordance with (d).

The fourth process according to the invention is carried out in exactly the same way as the second process according to the invention except that 4-nitrobenzyl halide is replaced as starting material by a commercial nitrobenzyl chloride isomer mixture which contains from 10 to 50% by weight and preferably from 30 to 40% by weight of 2-nitrobenzyl chloride and from 50 to 90% by weight and preferably from 50 to 60% by weight of 4-nitrobenzyl chloride, in addition to minor quantities of 3-nitrobenzyl chloride. "Minor quantities" are understood to be a maximum of 20% by weight and preferably a maximum of 15% by weight, based on the total weight. 3-nitrobenzyl chloride is always present in the starting mixture in a smaller quantity than the other two isomers, i.e. a minor quantity.

In the fourth process according to the invention, the end products obtained are diisocyanate mixtures which contain from 30 to 60% by weight and preferably from 40 to 50% by weight, based on the total mixture, of diisocyanates corresponding to the formula:

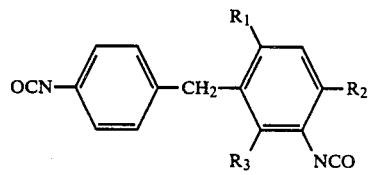

and from 10 to 40% by weight and preferably from 20 to 35% by weight, based on the total mixture, of diisocyanates corresponding to the formula:

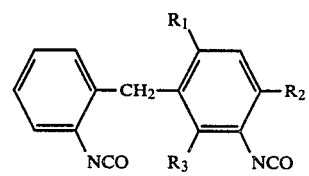

and up to 30% by weight, based on the total mixture, of other, analytically unidentifiable, methyl-substituted diisocyanatodiphenylmethane isomers. In these two formulae, as in the last four of the above formulae for the nitro compounds, one of the radicals $R_1$, $R_2$ or $R_3$ represents a methyl group while two of the radicals represent hydrogen.

The fifth process according to the invention comprises:

(a) reacting benzene with commercial nitrobenzyl chloride isomer mixtures obtained by nitrating 4-methyl benzyl chloride and containing from 10 to 25% by weight, based on the total mixture, of 2-nitro-4-methyl benzyl chloride and from 75 to 90% by weight, based on the total mixture, of 3-nitro-4-methyl benzyl chloride in the presence of a Friedel-Crafts catalyst to form a Friedel-Crafts condensate essentially containing mononitro compounds corresponding to the formulae:

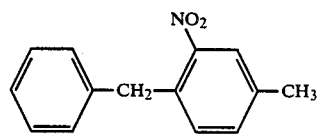

and, as the main component,

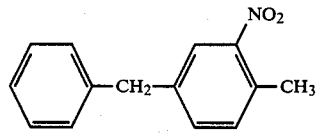

and removing the catalyst from the condensate;

(b) nitrating the condensate obtained in stage (a) to form a mixture of aromatic dinitro compounds containing nitro compounds corresponding to the following formulae:

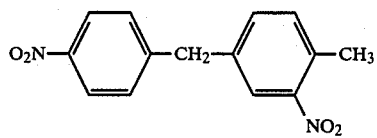

and

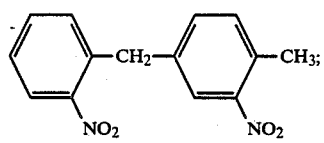

(c) hydrogenating or reducing the nitro groups of the nitro compounds obtained in stage (b) into the corresponding aromatic diamines;
(d) phosgenating the diamines obtained in stage (c) into the corresponding diisocyanates;
(e) optionally isolating the isomer mixture containing from 30 to 60% by weight, based on the total mixture, of 3,4'-isomers and from 10 to 40% by weight, base on the total mixture, of 3,2'-isomers and from 0 to 30% by weight, based on the total mixture, of other methyl-substituted diisocyanatodiphenylmethane isomers, free from secondary products by distillation from the mixture of aromatic amino compounds obtained in (c) before phosgenation and/or from the polyisocyanate mixture obtained in (d).

The fifth process according to the invention is carried out in exactly the same way as the fourth process according to the invention except that the commercial nitrobenzyl halide is replaced as starting material by a commercial 4-methyl nitrobenzyl chloride isomer mixture which contains from 10 to 25% by weight and preferably from 15 to 22% by weight of 4-methyl-2-nitrobenzyl chloride and from 75 to 90% by weight and preferably from 78 to 85% by weight of 4-methyl-3-nitrobenzyl chloride.

In the fifth process according to the invention, the end products formed are diisocyanate mixtures which contain from 30 to 60% by weight and preferably from 40 to 55% by weight, based on the total mixture, of diisocyanates corresponding to the formula:

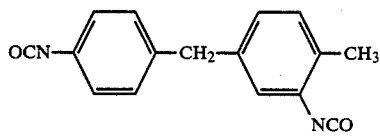

and from 10 to 40% by weight and preferably from 20 to 30% by weight, based on the total mixture, of diisocyanates corresponding to the formula:

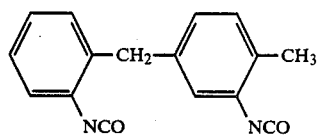

and up to 30% by weight, based on the total mixture, of other, analytically unidentifiable, methyl-substituted diisocyanatodiphenylmethane isomers.

The sixth process according to the invention for producing diisocyanates or diisocyanate mixtures, comprises:
(a) reacting a benzyl halide with tolune in the presence of a Friedel-Crafts catalyst or reacting benzyl alcohol with toluene in the presence of an acid catalyst to form a condensate corresponding to the following formula:

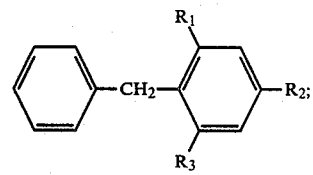

(b) dinitrating the methyl diphenylmethane isomer mixture corresponding to the above formula which is obtained in pure form from the condensate obtained in stage (a) by distillation;
(c) hydrogenating or reducing the nitro groups of the dinitro compounds obtained in stage (b) into the corresponding diamines;
(d) phosgenating the diamines obtained in stage (c) into the corresponding diisocyanates;
(e) optionally isolating the corresponding 3,4'-isomer which may be present in admixture with up to 40% by weight of 2',3-isomers and with up to 30% by weight, based on the total mixture, of other methyl-substituted diisocyanatodiphenylmethane isomers free from secondary products from the diamines obtained in (c) before phosgenation and/or from the diisocyanate mixtures obtained in (d).

In stage (a) of the sixth process according to the invention, the unsubstituted benzyl halide or benzyl alcohol is used instead of a nitrobenzyl halide.

Where a benzyl halide is used, the observations made in reference to the first and second processes according o the invention apply to stage (a), particularly in regard to the quantitative ratios between the reactants. However, it is preferred to use a molar ratio of toluene to benzyl chloride of from 5:1 to 15:1, a molar ratio of from 8:1 to 12:1 being particularly preferred. In the extreme case, however, the condensation reaction may be carried out in the gas phase at temperatures of up to 300° C. However, the preferred temperature for carrying out stage (a) lies within the ranges applied in stage (a) of the second process according to the invention.

Where benzyl alcohol is used as the starting material, the catalysts used are substantially involatile strong acids such as, for example, sulfuric acid, phosphoric acid or fixed-bed catalysts containing sulfonic acid groups (such as ion exchangers containing sulfonic acid groups) or inorganic solid catalysts having acid centers (such as tonsils or zeolites).

The observations made in reference to the reaction between benzyl chloride and toluene also apply in regard to the quantitative ratios between the reactants, i.e. in this case, too, the toluene is used in an excess corresponding to those observations. In this case, the reaction temperature is generally in the range from −20° to +300° C. and preferably in the range from 20° to 110° C. The condensate accumulating is freed from the catalyst, for example by washing with water in the case of homogeneous catalysis or by filtration in the case of heterogeneous catalysis and from the excess toluene by distillation and is subjected to stage (b) freed by distillation from small quantities of relatively high molecular weight condensates.

In stage (b), the condensate is subjected to a dinitration reaction in respect of which the observations made in reference to stage (b) of the second process according to the invention apply in principle, but with the difference that, in this case, a quantity of nitration acid corresponding to between about 2.0 and 2.5 mols of nitric acid is available for each mol of hydrocarbon to be nitrated.

The methyl-substituted dinitrodiphenylmethane isomers thus obtained are further processed in exactly the same way as described in reference to the first or second process according to the invention. In this case, too, the 4-methyl-3,4'-isomer may be prepared by partial crystallization at the nitro stage, as described in reference to the first process according to the invention.

In the sixth process according to the invention, diisocyanates corresponding to the formula:

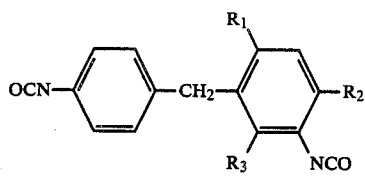

are obtained in admixture with up to 40% by weight and preferably in admixture with from 10 to 25% by weight, based on the total mixture, of diisocyanates corresponding to the formula

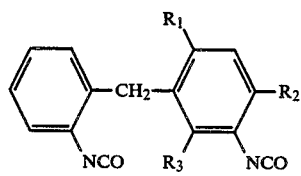

and with up to 30% by weight, based on the total mixture, of other methyl-substituted diisocyanatodiphenylmethane isomers. One of the radicals $R_1$, $R_2$ or $R_3$ represents a methyl group while two of the radicals represent hydrogen.

The seventh process according to the invention for producing diisocyanates or diisocyanate mixtures comprises:

(a) reacting a p-methyl benzyl halide with benzene in the presence of a Friedel-Crafts catalyst to form a hydrocarbon mixture of 4-methyl diphenylmethane and relatively high molecular weight condensates;

(b) dinitrating the 4-methyl diphenylmethane obtained in pure form by distillation from the hydrocarbon mixture obtained in stage (a);

(c) hydrogenating or reducing the nitro groups of the dinitro compound obtained in stage (b) into the corresponding aromatic diamino compound;

(d) phosgenating the diamines obtained in stage (c) into the corresponding diisocyanates;

(e) optionally isolating the corresponding 3,4'-isomers present in admixture with up to 30% by weight, based on the total mixture, of 2',3-isomers and with up to 30% by weight, based on the total mixture, of other methyl-substituted diisocyanatodiphenylmethane isomers free from secondary products from the diamines obtained in stage (c) before the phosgenation reaction and/or from the diisocyanates obtained in stage (d).

The observations made in reference to the sixth process according to the invention apply fully to the individual stages of this seventh process according to the invention.

In the seventh process according to the invention, 3,4'-diisocyanato-4-methyl diphenylmethane is obtained in admixture with up to 30% by weight and preferably with from 10 to 20% by weight, based on the total mixture, of 2',3-diisocyanato-4-methyl diphenylmethane and with up to 30% by weight, preferably with up to 20% by weight, based on the total mixture, of other, analytically unidentifiable, methyl-substituted diisocyanatodiphenylmethane isomers.

In the production of methyl-substituted diisocyanates or diisocyanate mixtures according to the invention, mixtures of isomers differing from one another in regard to the position of the methyl substituent are always formed, apart from the first process according to the invention using nitrobenzene and p-nitrotoluene and from the third and seventh process according to the invention. In most cases, the 3,4'-diisocyanato-4-methyl diphenylmethane according to the invention forms the main constituent. The position of the methyl substituent or the particular proportion of the respective isomers differing from one another through the position of the methyl substituent is of entirely minor importance in regard to the properties of the diisocyanate mixtures according to the invention and particularly in regard to their suitability as starting materials for the production of polyurethanes. The polyisocyanate mixtures according to the invention represent commercial mixtures which, as explained, often contain minor quantities, i.e. up to 30% by weight of constituents which cannot be clearly identified by analysis, particularly gas chromatography. The constituents in question are generally diisocyanatodiphenylmethane isomers containing a methyl substituent of which the NCO-groups are situated in the 2,4'-, 4,4'- or 3,3'-position, or mixtures of isomers such as these. However, the presence of these secondary products in the mixtures according to the invention, in the limits indicated, does not in any way adversely affect their favorable properties. All of the diisocyanates or diisocyanate mixtures according to the invention share the advantages over TDI and MDI mentioned at the beginning. The diisocyanates or diisocyanate mixtures according to the invention generally have a boiling point of from about 125° to 165° C. at a pressure of 0.1 mbar. The viscosity of the diisocyanates or diisocyanate mixtures according to the invention at 25° C. is generally in the range from 10 to 35 mPa.s. The diisocyanate mixtures according to the invention have no tendency towards crystallization at room temperature. Although the 4-methyl-3,4'-diisocyanatodiphenylmethane according to the invention has a melting point of approximately 42° C., it shows only a minimal tendency toward crystallization on storage at room temperature, in contrast to 4,4'-diisocyanatodiphenylmethane.

The diisocyanates or diisocyanate mixtures according to the invention, particularly the preferred methyl-substituted compounds or their mixtures, represent new, particularly valuable starting materials for the production of polyurethane plastics. The new diisocyanates or diisocyanate mixtures according to the invention may be used instead of TDI and/or MDI in all hitherto known processes for the production of polyurethane plastics using these known polyisocyanates.

EXAMPLES

Example 1

(a) 171.6 g (1 mol) of 4-nitrobenzyl chloride were dissolved at room temperature in 615 g (5 mols) of nitrobenzene, followed by the addition of 16.2 g (0.1 mol) of anhydrous iron (III) chloride.

The mixture was heated slowly with stirring to 100° C., left at that temperature for three hours and, after the evolution of hydrogen chloride had stopped, was stirred for one hour at 120° C. After cooling to room temperature, the reaction mixture was washed with 200 ml of dilute hydrochloric acid and three times with 200 ml of water. The dried organic phase was freed from the excess nitrobenzene in an oil pump vacuum. The residue weighed 236 g.

(b) 225 g of the residue from the condensation stage were dissolved in 500 ml of methanol, 50 g of fresh Raney nickel were added and the product was reduced with hydrogen at 50° C./50 bars until a constant pressure prevailed. On completion of the exothermic reaction, the reaction mixture was kept for one hour at 80° C. under a hydrogen pressure of 50 bars. The pressure was then released, the catalyst filtered off and methanol and water distilled off.

According to analysis by gas chromatography, the residue (173 g) consisted of 93% by weight of 3,4'-diaminodiphenylmethane, 7% by weight of trinuclear (>6% by weight) and higher (<1% by weight) compounds.

(c) The crude amine (172 g) was dissolved in 1.25 liters of monochlorobenzene and the resulting solution was slowly added dropwise with stirring and cooling at 0° C. to a solution of 400 g of phosgene in 1.25 liters of monochlorobenzene. The reaction mixture was then heated slowly while more phosgene was passed through and boiled under reflux for one hour.

The monochlorobenzene was then distilled off in a water jet vacuum and the isocyanate distilled under further reduced pressure (0.05 Torr). After first runnings of about 5 ml, 184 g (0.74 mol) of 3,4'-diisocyanatodiphenylmethane distilled over at 130° to 132° C. 19.5 g remained behind as distillation residue.

Example 2

(a) 171.6 g (1 mol) of 4-nitrobenzyl chloride were dissolved at room temperature in 685 g (5 mols) of 2-nitrotoluene, followed by the addition of 16.2 g (0.1 mol) of anhydrous iron (III) chloride.

The reaction mixture was heated slowly with stirring to 120° C. and left standing at that temperature until the evolution of hydrogen chloride had stopped. The reaction mixture was then stirred for one hour at 120° C.

After cooling to room temperature, the reaction mixture was diluted with 500 ml of methylene chloride, extracted once with 200 ml of semi-concentrated hydrochloric acid and washed three times with 500 ml of water. After drying, first the methylene chloride and then the excess 2-nitrotoluene were separated off, followed by distillation with steam.

According to analysis by gas chromatography, the residue (230 g) contained 2% by weight of low molecular weight constituents, 92% by weight of binuclear isomers and 6% by weight of trinuclear and higher isomers.

The binuclear fraction consisted of 61.1% by weight of 4-methyl-3,4'-dinitrodiphenylmethane and 38.9% by weight of 2-methyl-3,4'-dinitrodiphenylmethane.

(b) The crude product of the nitro stage was totally converted by reduction into the amine stage as in Example 1(b).

(c) The crude mixture of the amines was converted by phosgenation into the isocyanates as in Example 1(c).

The monochlorobenzene was then distilled off in a water jet vacuum and the isocyanate distilled under further reduced pressure (0.1 Torr). After several initial runnings (approximately 5 ml), a diisocyanate fraction (166 g; 0.63 mol) distilled over at 155°–165° C. for a distillation residue of 19 g.

According to analysis by gas chromatography, the diisocyanate fraction consisted of 39% by weight of 2-methyl-3,4'-diisocyanatodiphenylmethane and 61% by weight of 4-methyl-3,4'-diisocyanatodiphenylmethane.

Example 3

(a) 171.6 g (1 mol) of 4-nitrobenzyl chloride were melted together with 685 g (5 mols) of p-nitrotoluene and, after homogenization, 32.4 g (0.2 mol) of anhydrous iron(III) chloride were added to the resulting melt.

The reaction was carried out and the products worked up in the same way as Example 2a). A solid residue (224 g) was obtained.

(b) The crude product of the nitro stage was totally converted by reduction into the amine stage in the same way as in Example 1(b).

(c) The crude mixture of the amines was converted by phosgenation into the isocyanates in the same way as in Example 1(c).

The crude isocyanate (198 g) was distilled under reduced pressure. The main fraction (171.5 g=0.65 mol) consisted of 6-methyl-3,4'-diisocyanatodiphenylmethane ($Bp_{0.05}$ 143° C., colorless liquid).

Example 4

(a) 343.0 g (2 mols) of 4-nitrobenzyl chloride were dissolved in 920 g (10 mols) of dry toluene, followed by the addition of 32.4 g (0.2 mols) of anhydrous iron (III) chloride.

The solution was slowly heated with stirring to 80° C., kept at that temperature for five hours, boiled under reflux for one hour after the evolution of hydrogen chloride had stopped, poured into iced water after cooling and washed three times with 500 ml of water until free from acid.

After drying and removal of the excess toluene by distillation under normal pressure, the residue (430 g) was distilled under reduced pressure (0.5 Torr). 398.4 g (87.8% of the theoretical) of a low viscosity, yellow oil distilled over between 140° and 150° C.

(b) 340.5 g (1.5 mols) of the distilled mixture of the 4-nitromethyl diphenylmethanes were initially introduced in 400 ml of methylene chloride at 0° to 10° C. Nitration acid consisting of a mixture of 110 g (1.7 mols) of 98% $HNO_3$ and 170 g (1.7 mols) of 98% $H_2SO_4$ was added with stirring and cooling at that temperature. On completion of the addition, the mixture was stirred for thirty minutes at 10° C., after which the mixed acid was separated off. The remaining organic phase was washed twice with 200 ml of water, once with 5% sodium carbonate solution and twice more with water. The methylene chloride was then distilled off under normal pressure up to a sump temperature of 90° C. and the solvent residues were stipped out with steam. The resulting product was dehydrated in a water jet vacuum at 80° C. According to analysis by gas chromatography, it contained 2.4% by weight of mono-nitromethyl diphenylmethane, 91.7% by weight of dinitromethyl diphenylmethane and 5.9% by weight of trinitromethyl diphenylmethane.

(c) The crude product of the nitro stage (397 g) was totally converted by reduction into the amine stage in the same way as in Example 1b).

(d) The crude mixture of the amines (296 g) was converted by phosgenation into the isocyanates in the same way as in Example 1(c).

The monochlorobenzene was then distilled off in a water jet vacuum and the isocyanate distilled under further reduced pressure (0.1 Torr). After initial runnings of about 25 ml, a diisocyanate fraction (295.3 g; 1.12 mols) distilled over at 155°-165° C. The distillation residue weighed 52 g.

According to analysis by gas chromatography, the diisocyanate fraction consisted of approximately 80% by weight of 2-, 4- and 6-methyl-3,4'-diisocyanatodiphenylmethane and approximately 20% by weight of other isomers.

Example 5

(a) 171.5 g (1 mol) of 3-nitrobenzyl chloride were dissolved in 546 g (7 mols) of dry benzene, followed by the addition of 13 g (0.1 mol) of anhydrous aluminum chloride.

The reaction mixture was slowly heated until the benzene boiled under reflux. The evolution of hydrogen chloride which began at around 60° C. was over after about one hour, after which the mixture was stirred under reflux for another hour.

The mixture was worked up in the same way as in Example 4(a). During distillation of the residue left following removal of the benzene, 182 g (0.858 mol) of a fraction which, according to gas chromatography, consisted of 96% by weight of methanitrodiphenylmethane distilled over between 95° and 135° C./0.1–1.5 Torr. The distillation residue weighed 21 g.

(b) 213 g (1 mol) of 3-nitrodiphenylmethane were subjected to a second nitration as in Example 4(b) and the resulting product worked up. According to gas chromatography, the crude product (248 g) contained 1.6% by weight of mono-nitrodiphenylmethane, 96.2% by weight of dinitrodiphenylmethane and 2.2% by weight of trinitrodiphenylmethane.

(c) The crude product of the nitro stage was totally converted by reduction into the amine stage in the same way as in Example 1(b) (yield: 180.5 g). (d) The crude mixture of the amines was converted by phosgenation into the isocyanates in the same way as in Example 1(c) (yield 230 g).

The monochlorobenzene was then distilled off in a water jet vacuum and the isocyanate distilled under further reduced pressure (0.1 Torr). After first runnings of approximately 15 ml, which still contained chlorobenzene, a diisocyanate fraction of 199 g (0.8 mol) distilled over at 145°-160° C. The distillation residue weighed 17 g.

The diisocyanate fraction had the following composition according to gas chromatography: 22% by weight of 2,3'-diisocyanatodiphenylmethane, 5.2% by weight of 3,3'-diisocyanatodiphenylmethane and 72.8% by weight of 3,4'-diisocyanatodiphenylmethane.

Example 6

(a) 254 g (2 mols) of benzyl chloride were initially introduced with 295 g (3 mols) of 98% sulfuric acid in 400 ml of methylene chloride at a temperature of −5° C. 190 g (3 mols) of 100% nitric acid was then added dropwise with stirring and cooling over a period of 1.5 hours at −5° C. to 0° C. After the addition, the mixture was stirred for one hour at 0° C.

The nitration mixture was then stirred into 1.2 liters of ice water, the organic phase was separated off, washed twice with 500 ml of water, shaken with 300 ml of saturated sodium bicarbonate solution, washed once more with water and then dried over sodium sulfate.

The methylene chloride was distilled off at normal pressure. The residue was distilled under reduced pressure (0.1 Torr). 328 g of a mixture of the mono-nitrobenzyl chlorides distilled over at a head temperature of from 80° C. to 120° C. The distillation residue weighed 6 g so that, for further batches, distillation was omitted.

The isomer distribution of the main fraction was indirectly determined by reacting the mixture with benzene in accordance with example 4(a), but in the presence of equimolar quantities of anhydrous iron (III) chloride. The resulting mixture of mono-nitrodiphenylmethanes was found by gas chromatography to have the following composition: 33.7% by weight of 2-nitrodiphenylmethane, 11.6% by weight of 3-nitrodiphenylmethane and 54.2% by weight of 4-nitrodiphenylmethane.

920 g (10 mols) of dry toluene were initially introduced with 121.5 g (0.75 mol) of anhydrous iron (III) chloride at 60° C. A solution of 257.4 g (1.5 mols) of the mixture of the nitrobenzyl chlorides in 460 g (5 mols) of dry toluene was then slowly added dropwise with stirring and cooling (evolution of hydrogen chloride). On completion of the addition, the mixture was sitrred for. one hour at 80° C.

Further working up was carried out in the same way as in Example 4(a). A mixture of the mono-nitromethyl diphenylmethanes (296 g; 1.30 mols) distilled over between 115° and 140° C. under a pressure of 0.1-0.3 Torr (distillation residue: 39 g). This mixture could not be analyzed by gas chromatography.

(b) The distillate (295 g) of 6(a) was subjected to a second nitration and the resulting product worked up in accordance with Example 4(b). Yield: 341 g.

(c) The crude mixture of the nitro compounds was totally converted by reduction into the amine stage in accordance with Example 1(b). Yield: 251 g.

(d) The crude mixture of the amines was converted by phosgenation into the isocyanates in accordance with Example 1(c).

The monochlorobenzene was then distilled off in a water jet vacuum and the isocyanate distilled under further reduced pressure (0.1 Torr). After first runnings of approximately 18 ml, a diisocyanate fraction (251 g; 0.95 mol) distilled over at 155°–165° C. The distillation residue weighed 44 g.

According to gas chromatography, the diisocyanate fraction consisted of approximately 30% by weight of methyl-2′,3-diisocyanatodiphenylmethanes, approximately 54% by weight of methyl-3,4′-diisocyanatodiphenylmethanes, and approximately 25% by weight of other isomers, and accumulated in the form of a pale yellow, low viscosity oil (20 Cp) without any tendency toward crystallization (examined to 0° C.).

The content of 4-methyl-3,4′-diisocyanatodiphenylmethane amounted to approximately 31% by weight (main constituent).

Example 7

(a) 282 g (2 mols) of 4-methylbenzyl chloride were nitrated and worked up in the same way as in Example 6(a). Yield: 362 g of crude product.

As in 6(a), the crude product was reacted with benzene, worked up and distilled following removal of the benzene. A mixture of the mono-nitromethyl diphenylmethanes (372 g; 1.64 mols) was obtained at 0.1 Torr/115°–125° C. and, according to analysis by gas chromatography, consisted of approximately 19% by weight of 2-nitro-4-methyl diphenylmethane and approximately 81% by weight of 3-nitro-4-methyl diphenylmethane.

(b) The distilled mixture (340.5 g=1.5 mols) was subjected to a second nitration in accordance with Example 4(b). Yield: 396 g.

Analysis by gas chromatography produced the following composition: 1% by weight of mononitro-4-methyl diphenylmethane, 92% by weight of dinitro-4-methyl diphenylmethane and 7% by weight of trinitro-4-methyl diphenylmethane.

(c) The crude mixture of the nitro compounds was totally converted by reduction into the amine stage in accordance with Example 1b). Yield: 300 g.

(d) The crude mixture of the amines was totally converted by phosgenation into the isocyanates in accordance with Example 1(c).

The monochlorobenzene was then distilled off in a water jet vacuum and the isocyanate distilled under further reduced pressure (0.1 Torr). After initial runnings of approximately 15 ml which still contained chlorobenzene, a diisocyanate fraction (294 g=1.11 mols) distilled over at 155°–165° C. The distillation residue weighed 53 g.

According to gas chromatography, the diisocyanate fraction consisted of 25.2% by weight of 2′,3-diisocyanato-4-methyl diphenylmethane, 48.8% by weight of 3,4′-diisocyanato-4-methyl diphenylmethane and 26% by weight of other isomers, and accumulated in the form of a pale yellow, low viscosity oil.

Example 8

(a) 1.84 kg (20 mols) of dry toluene were initially introduced under nitrogen, followed by the addition of 2 g of anhydrous iron (III) chloride. 253 g (2 mols) of dry benzyl chloride were then added dropwise with stirring and refluxing, gaseous hydrogen chloride being given off. On completion of the addition, the mixture was stirred for thirty minutes, cooled and washed three times with 500 ml of water until free from acid. The excess toluene was then separated off from the organic phase by distillation under normal pressure up to a sump temperature of 150° C.

The hydrocarbon mixture (346 g) left behind consisted of 89 to 92% by weight of binuclear isomers, 8 to 10% by weight of trinuclear isomers and <2% by weight of higher constituents.

The binuclear fraction ($Bp_{0.1}$ 78°–80° C.) and then the trinuclear fraction ($Bp_{0.1}$ 150°–175° C.) were separated off by distillation under reduced pressure.

According to gas chromatography and NMR analysis, the binuclear fraction contaiined 44 to 45% by weight of 2-methyl diphenylmethane, 48 to 49% by weight of 4-methyl diphenylmethane and 6 to 8% by weight of 3-methyl diphenylmethane.

(b) 364 g (2 mols) of the mixture of the binuclear isomers of methyl diphenylmethane obtained in accordance with 8(a) were initially introduced in 800 ml of methylene chloride at 0° to 10° C. Nitration acid, consisting of a mixture of 290 g (4.5 mols) of 98% nitric acid and 450 g (4.5 mols) of 98% sulfuric acid, was added with stirring and cooling at that temperature. On completion of the addition, the mixture was stirred for thirty minutes at 10° C., after which the mixed acid was separated off. The organic phase was washed twice with 400 ml of water, once with 5% sodium carbonate solution and twice more with water. The methylene chloride was then distilled off under normal pressure up to a sump temperature of 90° C., after which the solvent residues were freed from water with steam in a water jet vacuum at 80° C. The residue contained 5% by weight of nitrotoluene, 2% by weight of mono-nitromethyl diphenylmethane, 90% by weight of dinitromethyl diphenylmethane, and 2% by weight of tri- and tetranitromethyl diphenylmethane.

The dinitro fraction consisted of 15 to 20% by weight of 2′,3-dinitromethyl diphenylmethane, 55 to 60% by weight of 3,4′-dinitromethyl diphenylmethane and up to 30% by weight of other isomers.

(c) 500 g of the crude mixture of the nitration stage were taken up in 1 liter of methanol, 100 g of fresh Raney nickel added and the mixture reduced at 50° C. under a hydrogen pressure of 50 bars. On completion of the exothermic reaction, the hydrogen pressure was kept at 50 bars for one hour at 60° C. The pressure was then released, the catalyst filtered off and methanol and water were distilled off.

The residue (381 g) was distilled under reduced pressure, initial runnings of approximately 10 g of a toluidine mixture containing residues of water initially distilling over.

Most of the amine mixture (352 g) distilled at 150° to 200° C. (0.1 Torr). The residue in the distillation flask weighed 19 g.

(d) 212 g (1 mol) of the mixture of the diaminomethyl diphenylmethanes, still containing approximately 1% of monoamine, were dissolved in 1.25 liters of monochlorobenzene and the resulting solution slowly added dropwise with stirring and cooling at 0° C. to a solution of 400 g of phosgene in 1.25 liters of monochlorobenzene. The reaction mixture was then slowly heated while more phosgene was passed through until the monochlorobenzene boiled under reflux and was then kept under reflux for one hour.

After the monochlorobenzene had been distilled off in a water jet vacuum, the isocyanate was distilled under a reduced pressure of 0.05 Torr. After first runnings of 5 g, the isomer mixture of the isocyanates (248 g, NCO-content, 31.7 g) was obtained at 155°-165° C. in the form of a pale yellow oil which remained liquid, even at 0° C. The distillation residue weighed 11 g.

The isomer distribution of the diisocyanate fraction corresponds to the isomer distribution of the dinitro fraction.

Example 9

(a) 1000 g of the crude mixture of nitro compounds obtained in accordance with Example 8(b) were stirred with 1 liter of ethanol at room temperature to form a crystal sludge which was then filtered under suction. The residue was recrystallized once from isopropanol. The residue of the crystallization step (250 g=0.92 mol) consisted of approximately 98% pure 3,4'-dinitro-4-methyl diphenylmethane (Mp 146°-147° C.).

(b) The dinitro compound was reduced to the amine compound in accordance with Example 7(c). The yield of distilled diamine amounted to 180 g (Bp$_{0.1}$ 195° C.) (0.85 mol≙92.4%).

(c) The diamine (145 g=0.68 mol) was converted into the isocyanate in accordance with Example 7(d). The yield after distillation (Bp$_{0.1}$ 158°-160° C.) amounted to 159 g (0.60 mol) of 3,4'-diisocyanato-4-methyl diphenylmethane.

According to gas chromatography, the product was 98.3% pure. The colorless oily liquid (viscosity at 25° C.=16 Cp) only crystallized after prolonged standing (Mp 41°-42° C.). The NCO-content amounted to 31.7% by weight.

Example 10

(a) 5.85 kg (75 mols) of dry benzene were initially introduced under nitrogen, followed by the addition of 1 g of anhydrous iron (III) chloride. A solution of 591 g (4.2 mols) of 4-methyl benzyl chloride in 702 g (9 mols) of benzene was then added dropwise over a period of two hours at a temperature of 60° C.

After the evolution of hydrogen chloride had stopped, the mixture was refluxed for one hour, cooled, washed three times with 1 liter of water until free from acid and the benzene distilled off under normal pressure from the organic phase.

The hydrocarbon mixture (approximately 700 g) left behind was distilled under reduced pressure (0.1 Torr). 294 g (38.5% of the theoretical) of 4-methyl diphenylmethane distilled over at 80° C. The residue consisted of trinuclear and higher material which, apart from a small residue, distilled at between 100° and 300° C.

(b) 273 g (1.5 mols) of 4-methyl diphenylmethane were converted into a mixture of nitro compounds as in Example 8(b) using the corresponding quantity of nitration acid. According to analysis by gas chromatography, the resulting product (392 g) contained 8% by weight of nitrotoluene, 1% by weight of mononitro-4-methyl diphenylmethane, 86.1% by weight of dinitro-4-methyl diphenylmethane and 5% by weight of trinitro-4-methyl diphenylmethane.

(c) The crude mixture of the nitration stage (290 g) was converted by reduction into the amine stage as in Examples 1(b) and 8(c). The amine mixture was distilled in a water jet vacuum at a temperature of up to 200° C. Yield: 195 g of crude amine.

(d) The crude mixture of the amines was totally converted into the isocyanates in accordance with Example 1(c) and 8(d).

After the monochlorobenzene had been distilled off in a water jet vacuum, the isocyanate was distilled at 0.1 Torr. After initial runnings of 15 ml, which still contained monochlorobenzene and even some product, the isomer mixture of the diisocyanates (274 g, NCO-content, 31.7%) distilled over at 155°-170° C. in the form of a pale yellow oil which, even at 0° C., did not show any tendency toward crystallization. The distillation residue weighed 43 g.

According to analysis by gas chromatography, the mixture consisted of 15.5% by weight of 2',3-diisocyanato-4-methyl diphenylmethane, 69.3% by weight of 3,4'-diisocyanato-4-methyl diphenylmethane and approximately 15% by weight of other isomers.

What is claimed is:

1. Diisocyanates corresponding to the formula:

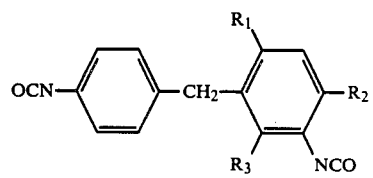

which may be present in admixture with 0 to 40% by weight, based on the total mixture, of diisocyanates corresponding to the formula:

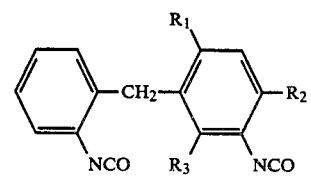

and optionally with 0 to 30% by weight, based on the total mixture, of other diisocyanatodiphenylmethane isomers which may be substituted; wherein two of the radicals $R_1$, $R_2$ and $R_3$ represent hydrogen and one of the radicals $R_1$, $R_2$ and $R_3$ represents a methyl group.

2. The diisocyanate of claim 1 corresponding to the formula:

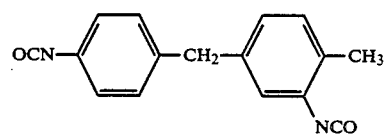

3. The diisocyanate of claim 1 corresponding to the formula:

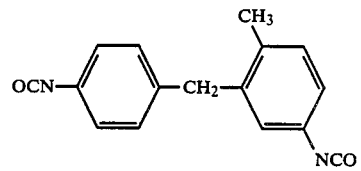

4. Diisocyanatodiphenylmethane isomer mixtures comprising from 30 to 60% by weight, based on the total mixture, of diisocyanates corresponding to the formula:

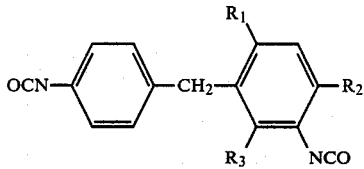

and from 10 to 40% by weight, based on the total mixture, of diisocyanates corresponding to the formula:

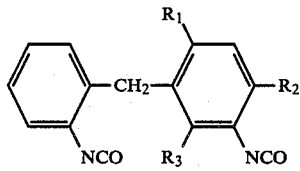

and from 0 to 30% by weight, based on the total mixture of other methyl-substituted diisocyanatodiphenylmethane isomers, wherein one of the radicals $R_1$, $R_2$ or $R_3$, in each of the formulae, represents a methyl group and the other two hydrogen.

5. Diisocyanatodiphenylmethane isomer mixtures comprising from 30 to 60% by weight, based on the total mixture, of diisocyanates corresponding to the formula:

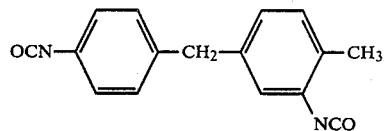

and from 10 to 40% by weight, based on the total mixture, of diisocyanates corresponding to the formula:

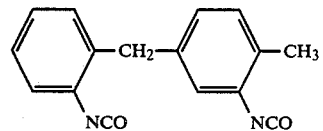

and from 0 to 30% by weight, based on the total mixture, of other methyl-substituted diisocyanatodiphenylmethane isomers.

6. Diisocyanatodiphenylmethane isomer mixtures comprising from 70 to 90% by weight based on the total mixture, of 3,4'-diisocyanato-2-, -4-, and/or -6-methyldiphenylmethane and from 10 to 30% by weight of other methyl-substituted diisocyanatodiphenylmethane isomers.

* * * * *